United States Patent
Okamoto et al.

(10) Patent No.: US 11,485,931 B2
(45) Date of Patent: Nov. 1, 2022

(54) ISOBUTYRIC ESTER COMPOUND HAVING FORMYLOXY GROUP AT α-POSITION, FRAGRANCE COMPOSITION, AND USE THEREOF AS FRAGRANCE

(71) Applicant: MITSUBISHI GAS CHEMICAL COMPANY, INC., Chiyoda-ku (JP)

(72) Inventors: Atsushi Okamoto, Niigata (JP); Eriko Kushida, Niigata (JP); Umi Yokobori, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 17/255,137

(22) PCT Filed: Jun. 26, 2019

(86) PCT No.: PCT/JP2019/025395
§ 371 (c)(1),
(2) Date: Dec. 22, 2020

(87) PCT Pub. No.: WO2020/004467
PCT Pub. Date: Jan. 2, 2020

(65) Prior Publication Data
US 2021/0269742 A1    Sep. 2, 2021

(30) Foreign Application Priority Data

Jun. 26, 2018 (JP) .............................. JP2018-121110
Nov. 28, 2018 (JP) .............................. JP2018-222718

(51) Int. Cl.
*C11B 9/00* (2006.01)
*C07C 69/67* (2006.01)

(52) U.S. Cl.
CPC ............ *C11B 9/0019* (2013.01); *C07C 69/67* (2013.01); *C11B 9/003* (2013.01); *C07C 2601/08* (2017.05)

(58) Field of Classification Search
CPC ....... C11B 9/0019; C11B 9/003; C07C 69/67; C07C 2601/08; C07C 2601/14
See application file for complete search history.

(56) References Cited

U.S. PATENT DOCUMENTS

| | | |
|---|---|---|
| 3,368,943 A | 2/1968 | Gilbert et al. |
| 4,498,996 A | 2/1985 | Klemarczyk |
| 2011/0064998 A1* | 3/2011 | Abe ............ H01M 6/168 429/188 |
| 2011/0097291 A1* | 4/2011 | Vial ............ C11B 9/0019 512/26 |

FOREIGN PATENT DOCUMENTS

| | | |
|---|---|---|
| EP | 2 251 926 A1 | 11/2010 |
| JP | 8-113795 A | 5/1996 |
| JP | 2011-524437 A | 9/2011 |
| JP | 2014-31331 A | 2/2014 |
| WO | WO 01/13740 A | 3/2001 |
| WO | WO 2009/113545 A1 | 9/2009 |
| WO | WO 2009/147565 A1 | 12/2009 |

OTHER PUBLICATIONS

International Search Report dated Aug. 27, 2019 in PCT/JP2019/025395 filed on Jun. 26, 2019, 1 page.
Extended European Search Report dated Jul. 14, 2021 in European Patent Application No. 19826918.5, 8 pages.

* cited by examiner

*Primary Examiner* — Yate' K Cutliff
(74) *Attorney, Agent, or Firm* — Oblon, McClelland, Maier & Neustadt, L.L.P.

(57) ABSTRACT

A fragrance composition comprising a compound represented by Formula (1) as an active ingredient:

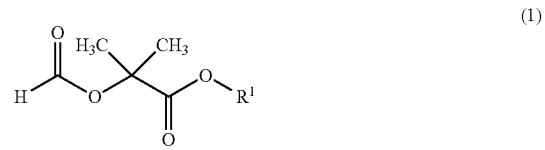

wherein, in Formula (1), $R^1$ represents a linear, branched, or cyclic alkyl group having 1 to 6 carbon atoms.

9 Claims, No Drawings

ISOBUTYRIC ESTER COMPOUND HAVING FORMYLOXY GROUP AT α-POSITION, FRAGRANCE COMPOSITION, AND USE THEREOF AS FRAGRANCE

TECHNICAL FIELD

The present invention relates to isobutyric ester compounds having a formyloxy group at the α-position, fragrance compositions, and uses thereof as a fragrance.

BACKGROUND ART

Isobutyric esters and isobutyric esters having a bond to oxygen have been reported to be useful as fragrances. For example, Patent Document 1 discloses that, as an isobutyric ester having a bond with oxygen at the α-position, a linear or branched alkyl ester having from 4 to 12 carbon atoms of α-alkoxyisobutyric acid is useful as a fragrance, including a description in that n-hexyl α-ethoxyisobutyrate has a lavender-like aroma.

On the other hand, Patent Document 2 discloses that, as isobutyric esters having a formyloxy group at the α-position, a methyl ester and an ethyl ester are useful as an additive component of a non-aqueous electrolyte solution for lithium batteries, but there is no description about the aroma characteristics thereof, fragrance compositions comprising the same, and further, methods for use as a fragrance.

CITATION LIST

Patent Documents

Patent Document 1: U.S. Pat. No. 3,368,943
Patent Document 2: WO No. 2009/113545

DISCLOSURE OF THE INVENTION

Technical Problem

An object to be solved by the present invention is to provide an isobutyric ester compound having a formyloxy group at the α-position, which is useful as a fragrance and a fragrance ingredient. Further, another object to be solved by the present invention is to provide a fragrance composition containing an isobutyric ester compound having a formyloxy group at the α-position as an active ingredient and use of the compound as a fragrance.

Solution to Problem

The present inventors have synthesized various compounds and have made a diligent research of the aromas thereof. Thus, the present inventors discovered that particular ester compounds of isobutyric acid having a formyloxy group at the α-position are useful as fragrances and fragrance ingredients.

That is, the present invention is as follows.
<1> A fragrance composition comprising a compound represented by Formula (1) as an active ingredient:

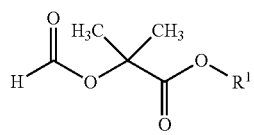

(1)

wherein, in Formula (1), $R^1$ represents a linear, branched, or cyclic alkyl group having 1 to 6 carbon atoms.

<2> The fragrance composition according to <1>, wherein, in Formula (1), $R^1$ is selected from the group consisting of a methyl group, an ethyl group, a n-propyl group, an isopropyl group, a n-butyl group, an isobutyl group, and a cyclopentyl group.

<3> Use of a compound represented by Formula (1) as a fragrance:

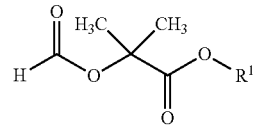

(1)

wherein, in Formula (1), $R^1$ represents a linear, branched, or cyclic alkyl group having 1 to 6 carbon atoms.

<4> The use according to <3>, wherein, in Formula (1), $R^1$ is selected from the group consisting of a methyl group, an ethyl group, a n-propyl group, an isopropyl group, a n-butyl group, an isobutyl group, and a cyclopentyl group.

<5> The use according to <3> or <4>, wherein the compound represented by Formula (1) imparts a mint-like or fruit-like scent.

<6> The use according to <3> or <4>, wherein the compound in which $R^1$ is a methyl group in Formula (1) imparts a damascone-like fruity-tone, floral-tone, or woody-tone scent.

<7> A compound, represented by Formula (2):

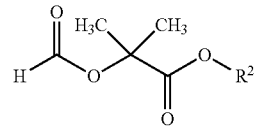

(2)

wherein, in Formula (2), $R^2$ represents a linear, branched, or cyclic alkyl group having 3 to 6 carbon atoms.

<8> The compound according to <7>, wherein, in Formula (2), $R^2$ is selected from the group consisting of a n-propyl group, an isopropyl group, a n-butyl group, an isobutyl group, and a cyclopentyl group.

<9> The compound according to <7> or <8>, wherein, in Formula (2), $R^2$ is a n-propyl group.

<10> The compound according to <7> or <8>, wherein, in Formula (2), $R^2$ is an isopropyl group.

<11> The compound according to <7> or <8>, wherein, in Formula (2), $R^2$ is a n-butyl group.

<12> The compound according to <7> or <8>, wherein, in Formula (2), $R^2$ is an isobutyl group.

<13> The compound according to <7> or <8>, wherein, in Formula (2), $R^2$ is a cyclopentyl group.

Advantageous Effects of Invention

According to the present invention, it is possible to provide an isobutyric ester compound having a formyloxy group at the α-position, useful as a fragrance and a fragrance ingredient. Further, according to the present invention, it is possible to provide a fragrance composition containing an isobutyric ester compound having a formyloxy group at the α-position as an active ingredient and use of the compound as a fragrance.

DESCRIPTION OF EMBODIMENTS

Fragrance Composition and Use

A fragrance composition of the present invention comprises a compound represented by Formula (1) below as an active ingredient. Furthermore, use of the present invention is use of the compound represented by Formula (1) below as a fragrance.

The present invention will be described in detail hereinbelow.

Compound Represented by Formula (1)

The compound to be used in the fragrance composition of the present invention and the use of the present invention is represented by Formula (1) below:

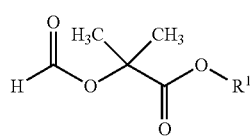

(1)

wherein, in Formula (1), $R^1$ represents a linear, branched, or cyclic alkyl group having from 1 to 6 carbon atoms.

In Formula (1), specific examples of $R^1$ include a methyl group, an ethyl group, a n-propyl group, an isopropyl group, a n-butyl group, an isobutyl group (2-methylpropyl group), a sec-butyl group (1-methylpropyl group), a tert-butyl group, a n-pentyl group, a 1-methylbutyl group (2-pentyl group), a 2-methylbutyl group, a 3-methylbutyl group, a neopentyl group (2,2-dimethylpropyl group), a 2-methylbutan-2-yl group, a 1-ethylpropyl group (3-pentyl group), a 3-methylbutan-2-yl group, a n-hexyl group, a 1-methylpentyl group (2-hexyl group), a 2-methylpentyl group, a 3-methylpentyl group, a 4-methylpentyl group, a 2-methylpentan-2-yl group, a 2,2-dimethylbutyl group, a 3,3-dimethylbutyl group, a 3-methylpentan-2-yl group, a 2,3-dimethylbutyl group, a 4-methylpentan-2-yl group, a 3-hexyl group, a 2-ethylbutyl group, a 2,3-dimethylbutan-2-yl group, a 3,3-dimethylbutan-2-yl group, a 4-methylpentan-3-yl group, a cyclopropyl group, a cyclobutyl group, a cyclopentyl group, and a cyclohexyl group.

When the $R^1$ group has one or more asymmetric carbons, the compound represented by Formula (1) comprises any one of optical isomers resulting from the asymmetric carbon or a mixture of the isomers at any proportion.

The compound represented by Formula (1), which is useful as a fragrance and a fragrance ingredient, has a mint-like or fruit-like aroma as well as simultaneously exhibits an aroma of a floral tone, herbal tone, woody tone, spicy tone, or the like due to the difference in the alkyl groups ($R^1$) of the ester moiety.

Particularly preferably, $R^1$ is a methyl group.
Particularly preferably, $R^1$ is an ethyl group.
Particularly preferably, $R^1$ is a n-propyl group.
Particularly preferably, $R^1$ is an isopropyl group.
Particularly preferably, $R^1$ is a n-butyl group.
Particularly preferably, $R^1$ is an isobutyl group.
Particularly preferably, $R^1$ is a cyclopentyl group.

In an embodiment of the present invention, examples of the compound represented by Formula (1) include a compound represented by any of Formulas (1-1) to (1-36) below, and particularly preferable compounds include compounds represented by any of Formulas (1-1) to (1-7) below.

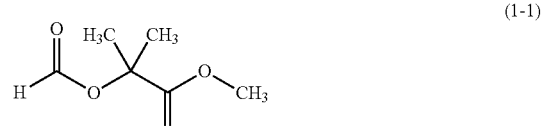

(1-1)

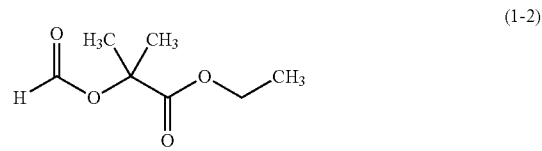

(1-2)

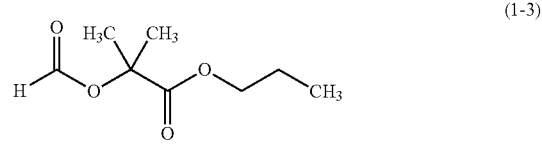

(1-3)

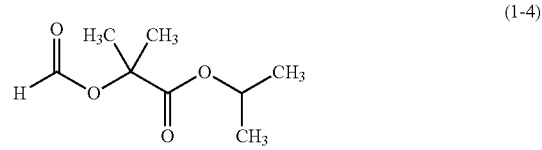

(1-4)

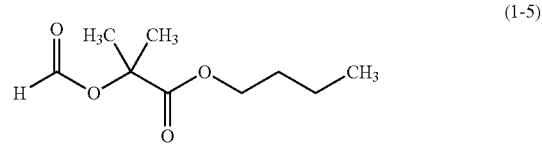

(1-5)

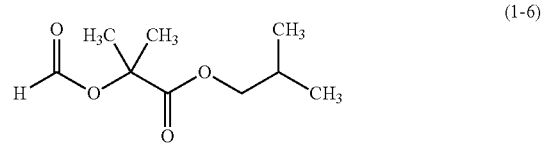

(1-6)

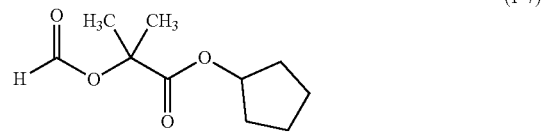

(1-7)

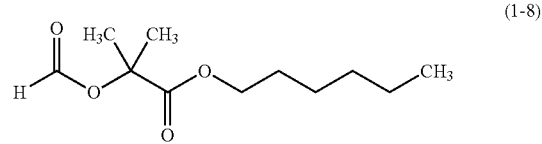

(1-8)

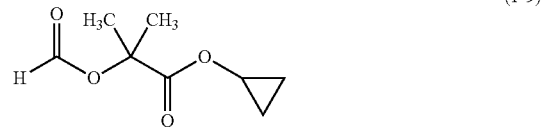

(1-9)

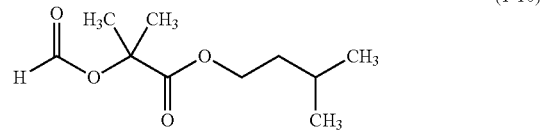

(1-10)

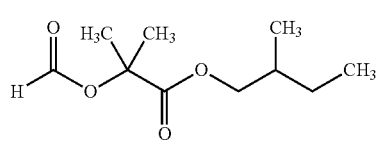 (1-11)
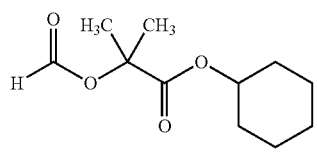 (1-12)
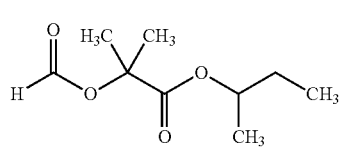 (1-13)
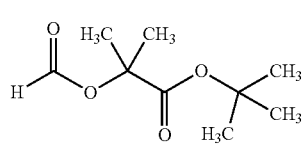 (1-14)
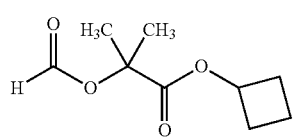 (1-15)
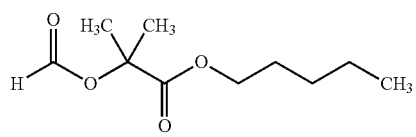 (1-16)
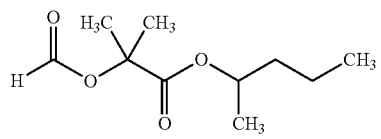 (1-17)
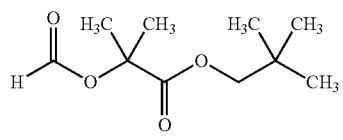 (1-18)
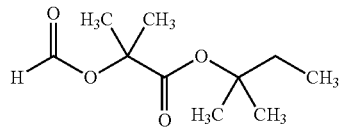 (1-19)
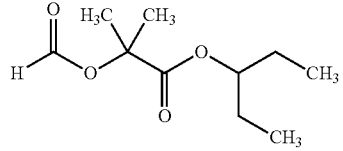 (1-20)
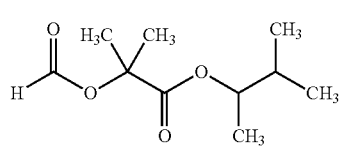 (1-21)
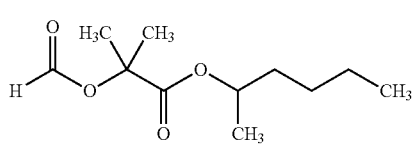 (1-22)
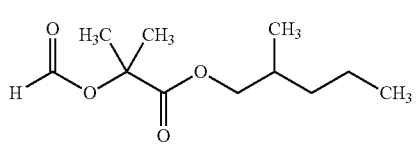 (1-23)
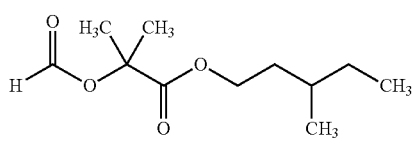 (1-24)
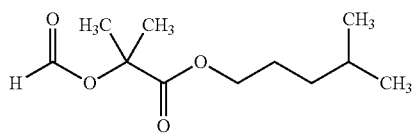 (1-25)
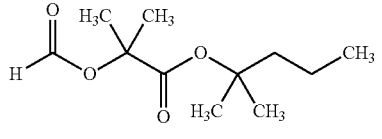 (1-26)
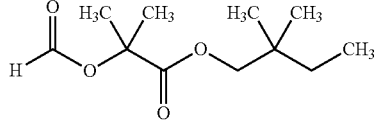 (1-27)
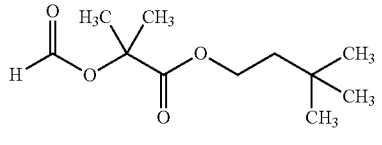 (1-28)
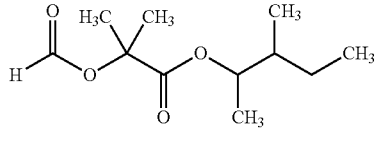 (1-29)
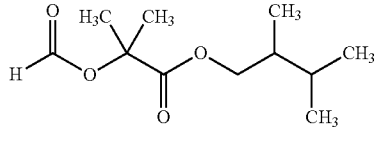 (1-30)
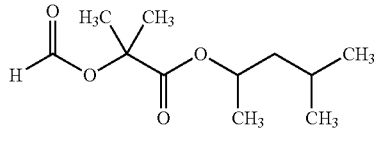 (1-31)
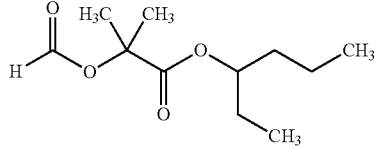 (1-32)

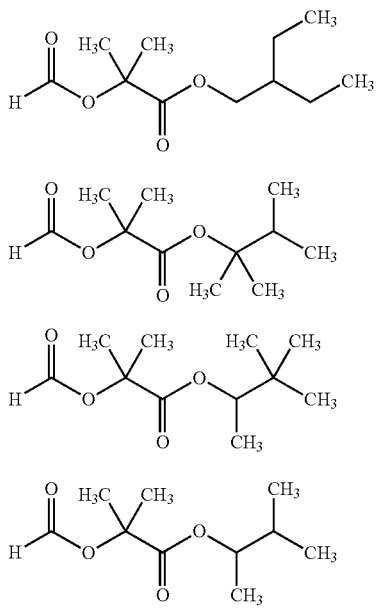

In recent years, there is a trend to focus more on the toxicity and environmental impact of chemicals, and fragrances or fragrance compositions are no exception. There is an increase in the number of cases where a fragrance which has been used in the past is severely restricted in usage conditions or is prohibited from use due to their sensitization properties to a human body, tendency to accumulate in the environment, and the like. Thus, there is a strong demand for a fragrance and a fragrance composition having a lower environmental impact. Accordingly, the fragrance ingredient preferably has excellent biodegradability.

The compound represented by Formula (1) contains a compound excellent in biodegradability, and from the perspective of biodegradability, $R^1$ is preferably a group selected from the group consisting of a methyl group, an ethyl group, a n-propyl group, an isopropyl group, a n-butyl group, an isobutyl group, and a cyclopentyl group.

The compound represented by Formula (1) is useful as a fragrance because the compound has an excellent aroma as described below. Generally, a fragrance is rarely used alone, and often used in a fragrance compound (fragrance composition) produced by compounding a plurality of fragrances in accordance with the purpose. The compound represented by Formula (1) is useful as a fragrance (also called a "fragrance ingredient") to be blended in a fragrance compound (fragrance composition), and the fragrance composition of the present invention contains the compound represented by Formula (1) as an active ingredient. As the fragrance, one of the compounds represented by Formula (1) above may be used alone or two or more of the compounds may be used in combination.

Additionally, the compound represented by Formula (1) may include a small amount of impurities, by-products, contaminants, and the like as long as the effects of the present invention are not compromised.

The compound represented by Formula (1) has a mint-like or fruit-like aroma as well as an aroma of floral-tone, herbal-tone, woody-tone, spicy-tone, or like, and also is excellent in diffusivity. Further, the compound represented by Formula (1-1) has a damascone-like fruity-tone, floral-tone, or woody-tone aroma, and also is excellent in diffusivity.

The compound represented by Formula (1) may be used alone as a fragrance and added to various perfumery and cosmetics, healthcare and sanitary materials as well as medicinal supplies, household goods, foods, and the like to thereby impart an aroma thereto. Alternatively, the compound represented by Formula (1) may be mixed with another fragrance ingredient or the like to prepare a fragrance composition (fragrance compound) described below, which may be blended into a variety of products to impart an aroma. Among these, from the perspective of obtaining an intended aroma, it is preferred that the compound represented by Formula (1) be blended in a fragrance composition as a fragrance ingredient to prepare a fragrance composition containing the compound represented by Formula (1) as an active ingredient and the fragrance composition be blended in a product to perfume the product.

Additionally, the compound represented by Formula (1) is preferably used as a fragrance and is more preferably used to impart a mint-like or fruit-like scent. Furthermore, the compound represented by Formula (1-1) is more preferably used to impart a damascone-like fruity-tone, floral-tone, or woody-tone scent.

Fragrance Composition

The fragrance composition (fragrance compound) of the present invention contains the compound represented by Formula (1) as an active ingredient. Note that the fragrance composition is not particularly limited as long as it contains at least one compound represented by Formula (1), and two or more compounds represented by Formula (1) may be included.

The fragrance composition according to an embodiment of the present invention is only required to contain the compound represented by Formula (1) as an active ingredient, and other ingredients are not particularly limited. However, the fragrance composition preferably contains another fragrance ingredient (hereinafter, also referred to as a "known fragrance").

Note that the "fragrance composition (fragrance compound)" is a composition that is added to various perfumery and cosmetics, medicinal supplies, foods, beverages, and the like to impart an aroma thereto, or a composition that is used as it is in a perfume or the like. The fragrance composition may contain an additive such as a solvent, as required, in addition to the known fragrance.

The amount of the compound represented by Formula (1) blended depends on the type of the compound, the type of aroma intended, the intensity of the aroma, and the like. The amount of the compound represented by Formula (1) in the fragrance composition is preferably 0.001 mass % or greater, more preferably 0.01 mass % or greater, even more preferably 0.1 mass % or greater, and preferably 90 mass % or less, more preferably 70 mass % or less, and even more preferably 50 mass % or less.

The known fragrance is not particularly limited as long as it is a known fragrance component, and a wide range of fragrances can be used. For example, one or two or more of the following fragrances can be selected and used at any mixing ratio.

Examples thereof include hydrocarbons such as limonene, α-pinene, β-pinene, terpinene, cedrene, longifolene, and valencene; alcohols such as linalool, citronellol, geraniol, nerol, terpineol, dihydromyrcenol, ethyllinalool, farnesol, nerolidol, cis-3-hexenol, cedrol, menthol, borneol, β-phenylethyl alcohol, benzyl alcohol, phenyl hexanol, 2,2,6-trimethylcyclohexyl-3-hexanol, 1-(2-t-butylcyclohexyloxy)-2- butanol, 4-isopropylcyclohexane methanol, 4-t-butylcyclohexanol, 4-methyl-2-(2-methylpropyl)tetrahydro-2H-pyran-4-ol, 2-methyl-4-(2,2,3-trimethyl-3-cyclopenten-1-yl)-2-butene-1-ol, 2-ethyl-4-(2,2,3-trimethyl-3-cyclopenten-1-yl)-2-buten-1-ol, isocamphylcyclohexanol, and 3,7-dimethyl-7-methoxyoctane-2-ol; phenols such as eugenol, thymol, and vanillin; esters such as linalyl formate, citronellyl formate, geranyl formate, n-hexyl acetate, cis-3-hexenyl acetate, linalyl acetate, citronellyl acetate, geranyl acetate, neryl acetate, terpinyl acetate, nopyl acetate, bornyl acetate, isobronyl acetate, o-t-butylcyclohexyl acetate, p-t-butylcyclohexyl acetate, tricyclodecenyl acetate, benzyl acetate, styralyl acetate, cinnamyl acetate, dimethylbenzylcarbinyl acetate, 3-pentyltetrahydropyran-4-yl acetate, citronellyl propionate, tricyclodecenyl propionate, allylcyclohexyl propionate, ethyl-2-cyclohexyl propionate, benzyl propionate, citronellyl butyrate, dimethylbenzylcarbinyl n-butyrate, tricyclodecenyl isobutyrate, methyl-2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyldihydro jasmonate, methyl-2,4-dihydroxy-3,6-dimethyl benzoate, ethylmethylphenyl glycidate, methyl anthranilate, and FRUITATE; aldehydes such as n-octanal, n-decanal, n-dodecanal, 2-methylundecanal, 10-undecenal, citronellal, citral, hydroxycitronellal, dimethyl tetrahydrobenzaldehyde, 4(3)-(4-hydroxy-4-methylpentyl)-3-cyclohexene-1-carboaldehyde, 2-cyclohexyl propanal, p-t-butyl-α-methylhydrocinnamic aldehyde, p-isopropyl-α-methylhydrocinnamic aldehyde, p-ethyl-α,α-dimethylhydrocinnamic aldehyde, α-amylcinnamicaldehyde, α-hexylcinnamic aldehyde, piperonal, and α-methyl-3,4-methylenedioxyhydrocinnamic aldehyde; ketones such as methylheptenone, 4-methylene-3,5,6,6-tetramethyl-2-heptanone, amylcyclopentanone, 3-methyl-2-(cis-2-pentene-1-yl)-2-cyclopentene-1-on, methylcyclopentenolone, rose ketones, γ-methylionone, α-ionone, carbone, menthone, camphor, nootkatone, benzylacetone, anisylacetone, methyl-β-naphthylketone, 2,5-dimethyl-4-hydroxy-3(2H)-furanone, maltol, 7-acetyl-1,2,3,4,5,6,7,8-octahydro-1,1,6,7-tetramethyl naphthalene, muscone, civetone, cyclopentadecanone, and cyclohexedecanone; acetals and ketals such as acetoaldehyde ethylphenylpropyl acetal, citraldiethyl acetal, phenylacetoaldehyde glycerin acetal, and ethylacetoacetate ethyleneglycol ketals; ethers such as anethole, β-naphthylmethyl ether, β-naphthylethyl ether, limonene oxide, rose oxide, 1,8-cineol, and racemic or photoactive dodecahydro-3a,6,6,9a-tetramethylnaphtho[2,1-b]furane; nitriles such as citronellyl nitrile; lactones such as γ-nonalactone, γ-undecalactone, σ-decalactone, γ-jasmolactone, coumarin, cyclopentadecanolide, cyclohexadecanolide, ambrettolide, ethylene brassylate, and 11-oxahexadecanolide; natural essential oils and natural extracts of orange, lemon, bergamot, mandarin, peppermint, spearmint, lavender, chamomile, rosemary, eucalyptus, sage, basil, rose, geranium, jasmine, ylang-ylang, anise, clove, ginger, nutmeg, cardamom, cedar, Japanese cypress, sandalwood, vetiver, patchouli, and labdanum; and other fragrance materials such as synthetic fragrances.

In addition, the fragrance composition may also contain, as components besides the fragrance ingredients, a surfactant such as polyoxyethylene lauryl sulfate ether; a solvent such as dipropylene glycol, diethyl phthalate, ethylene glycol, propylene glycol, methyl myristate, triethyl citrate, or the like; an antioxidant; a coloring agent, and the like.

The compound represented by Formula (1), which has a mint-like or fruit-like aroma and simultaneously has an aroma of a floral tone, a herbal tone, a woody tone, a spicy tone, or the like, can impart a natural floral tone, herbal tone, woody tone, or spicy tone in addition to the mint tone or fruit tone when combined with a known fragrance. Thus, the compound is usefully added to various perfumery and cosmetics, healthcare and sanitary materials as well as to medicinal supplies, household goods, foods, and the like to thereby impart an aroma thereto. The isobutyric ester according to an embodiment of the present invention represented by Formula (1-1) is usefully combined with a known fragrance or the like to thereby impart an aroma because of having a damascone-like fruity-tone, floral-tone, or woody-tone aroma.

Examples of products to which a fragrance composition containing the compound represented by Formula (1) can be added to impart an aroma and improve the aroma of the blend object include various products such as perfumery and cosmetics, health and sanitary materials, miscellaneous goods, beverages, foods, quasi-pharmaceutical products, and medicinal supplies; the fragrance composition can be used as an aroma component in, for example, fragrance products such as perfumes and colognes; hair cosmetics such as shampoos, rinses, hair tonics, hair creams, mousses, gels, pomades, sprays, and the like; skin cosmetics such as skin lotions, essences, creams, milky lotions, packs, foundations, face powders, lipsticks, and various make-up products; various health and sanitary detergents such as dish washing detergents, laundry detergents, softeners, disinfecting detergents, anti-odor detergents, indoor fragrances, furniture cares, glass cleaners, furniture cleaners, floor cleaners, disinfectants, insecticides, bleaching agents, bactericides, repellants, and the like; quasi-pharmaceutical products such as toothpastes, mouthwashes, bath additives, antiperspirant products, and perming liquids; miscellaneous goods such as toilet paper and tissue paper; medicinal supplies; foods, and the like.

The amount of the fragrance composition blended in the product is not particularly limited, and the amount of the fragrance composition blended can be selected over a wide range, depending on the type, nature, and sensory benefits of the product to be perfumed. For example, the amount may be 0.00001 mass % or greater, preferably 0.0001 mass % or greater, and more preferably 0.001 mass % or greater. In the case of a fragrance such as perfume or the like, for example, the amount may be 100 mass %, preferably 80 mass % or less, more preferably 60 mass % or less, and even more preferably 40 mass % or less.

Compound Represented by Formula (2)

A compound according to an embodiment of the present invention is represented by Formula (2). The compound represented by Formula (2) below is also referred to as the "isobutyric ester according to an embodiment of the present invention" or the "compound according to an embodiment of the present invention".

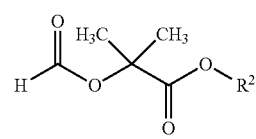

(2)

wherein, in Formula (2), $R^2$ represents a linear, branched, or cyclic alkyl group having 3 to 6 carbon atoms.

In Formula (2), specific examples of $R^2$ include a n-propyl group, an isopropyl group, a n-butyl group, an isobutyl group (2-methylpropyl group), a sec-butyl group (1-methylpropyl group), a tert-butyl group, a n-pentyl group, a 1-methylbutyl group (2-pentyl group), a 2-methylbutyl group, a 3-methylbutyl group, a neopentyl group (2,2-dimethylpropyl group), a 2-methylbutan-2-yl group, a 1-ethylpropyl group (3-pentyl group), a 3-methylbutan-2-yl group, a n-hexyl group, a 1-methylpentyl group (2-hexyl group), a 2-methylpentyl group, a 3-methylpentyl group, a 4-methylpentyl group, a 2-methylpentan-2-yl group, a 2,2-dimethylbutyl group, a 3,3-dimethylbutyl group, a 3-methylpentan-2-yl group, a 2,3-dimethylbutyl group, a 4-methylpentan-2-yl group, a 3-hexyl group, a 2-ethylbutyl group, a 2,3-dimethylbutan-2-yl group, a 3,3-dimethylbutan-2-yl group, a 4-methylpentan-3-yl group, a cyclopropyl group, a cyclobutyl group, a cyclopentyl group, and a cyclohexyl group.

When the $R^2$ group has one or more asymmetric carbons, the compound represented by Formula (2) comprises any one of optical isomers resulting from the asymmetric carbon or a mixture of the isomers at any proportion.

For the isobutyric ester according to an embodiment of the present invention, in Formula (2), $R^2$ is particularly preferably selected from the group consisting of a n-propyl group, an isopropyl group, a n-butyl group, an isobutyl group, and a cyclopentyl group.

That is, the isobutyric ester according to an embodiment of the present invention is particularly preferably the following compound.

In Formula (2), $R^2$ is a n-propyl group.
In Formula (2), $R^2$ is an isopropyl group.
In Formula (2), $R^2$ is a n-butyl group.
In Formula (2), $R^2$ is an isobutyl group.
In Formula (2), $R^2$ is a cyclopentyl group.

A compound preferred as the isobutyric ester according to an embodiment of the present invention is a compound represented by any of Formulas (2-1) to (2-34) below, and particularly preferred is a compound represented by any of Formulas (2-1) to (2-5).

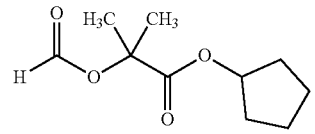
(2-1)

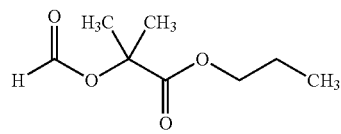
(2-2)

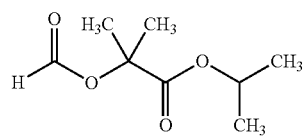
(2-3)

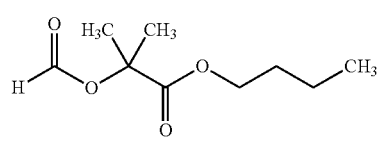
(2-4)

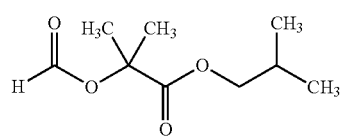

-continued

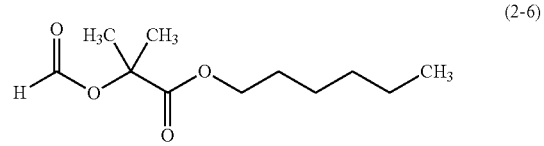
(2-5)

(2-6)

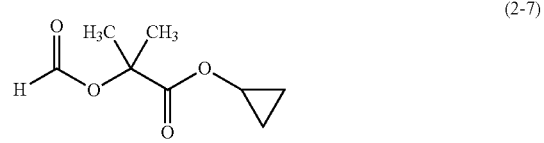
(2-7)

(2-8)

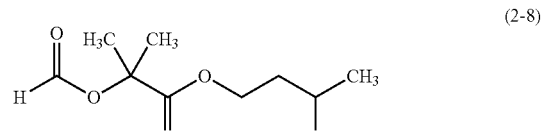
(2-9)

(2-10)

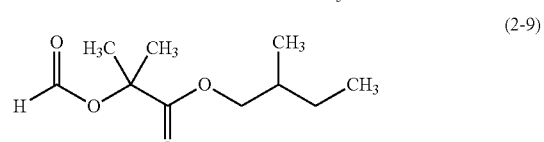
(2-11)

(2-12)

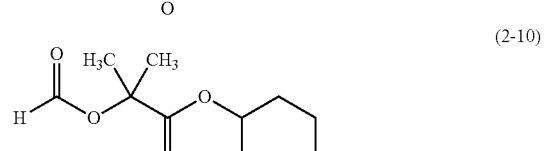
(2-13)

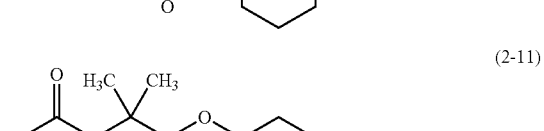
(2-14)

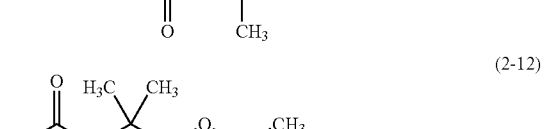
(2-15)

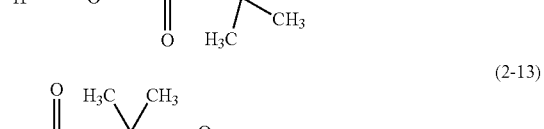

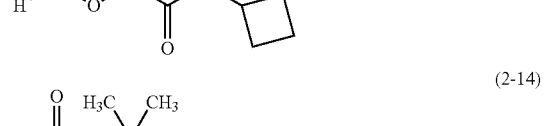

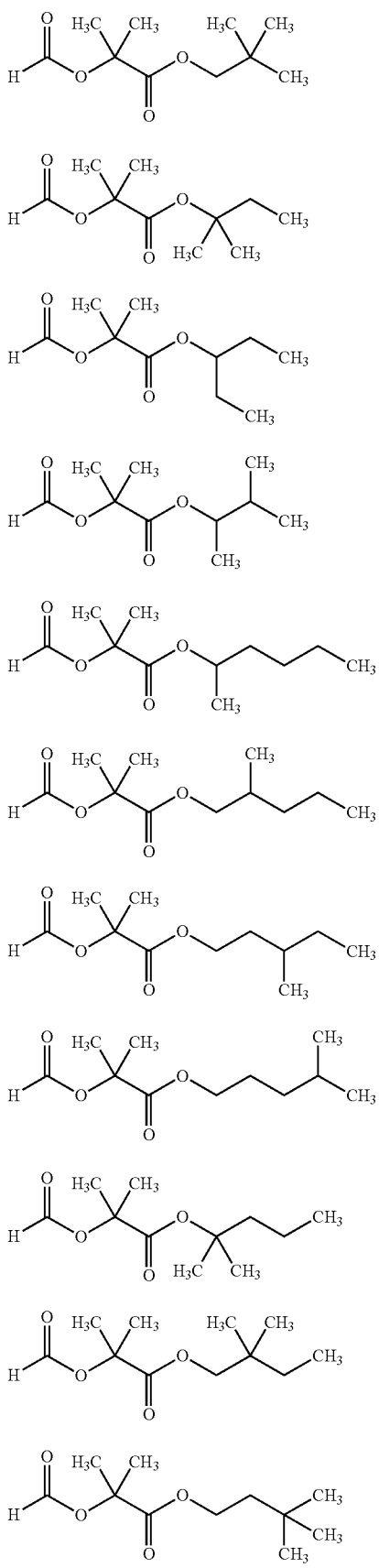
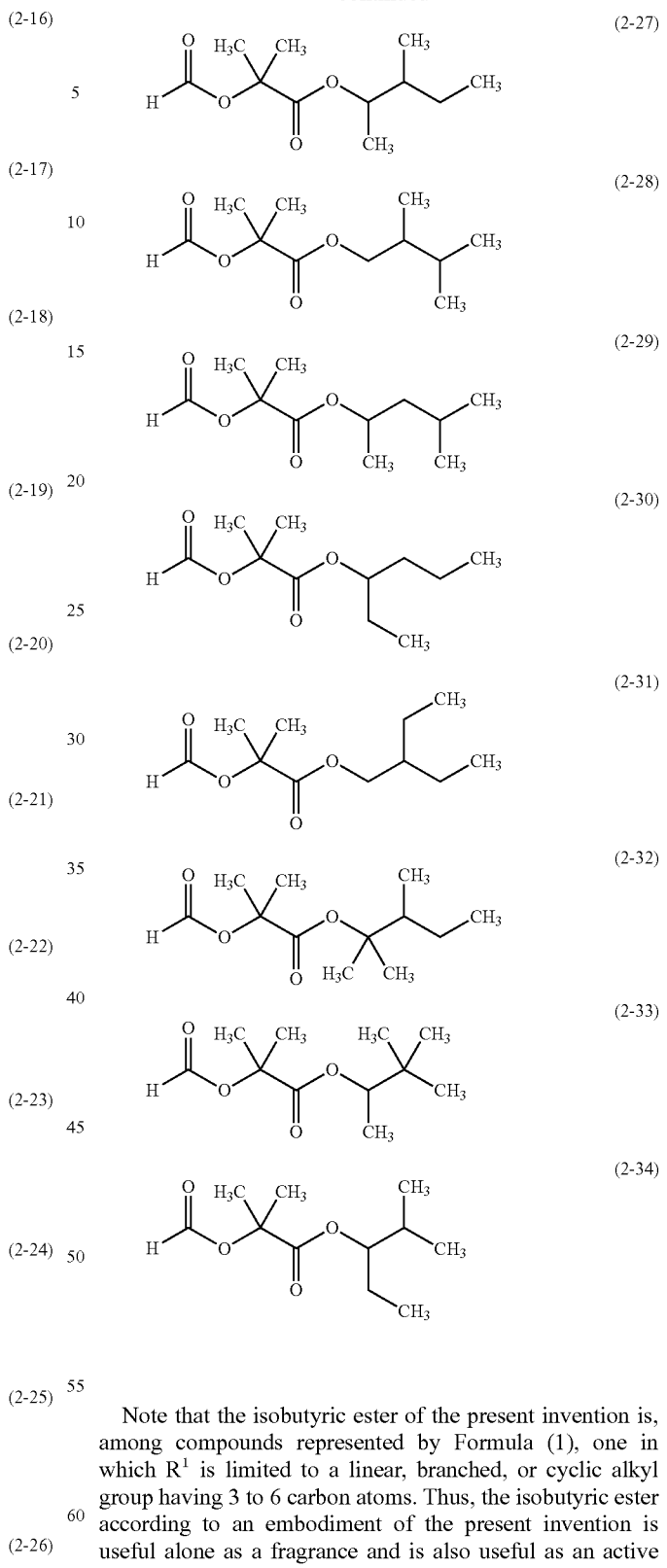

Note that the isobutyric ester of the present invention is, among compounds represented by Formula (1), one in which $R^1$ is limited to a linear, branched, or cyclic alkyl group having 3 to 6 carbon atoms. Thus, the isobutyric ester according to an embodiment of the present invention is useful alone as a fragrance and is also useful as an active ingredient for a fragrance composition.

Additionally, the isobutyric ester according to an embodiment of the present invention is preferably used as a fragrance and is more preferably used to impart a mint-like or fruit-like scent.

Method for Producing Isobutyric Ester According to Embodiment of Present Invention and Compound Represented by Formula (1)

The production method of the isobutyric ester according to an embodiment of the present invention represented by Formula (2) and the compound represented by Formula (1) is not particularly limited and may be appropriately selected from known methods and used.

Examples thereof include a method including reacting an α-hydroxyisobutyric ester with a formylating agent in the presence or absence of a catalyst to formylate the hydroxyl group at the α-position. Examples of the formylating agent to be used include carboxylic acids such as formic acid, carboxylic anhydrides such as formic anhydride and formic acetic anhydride, and carboxylic halides such as formyl chloride and formyl bromide. In addition, two or more formylating agents selected from these may be used in combination at any ratio.

The reaction formula when a carboxylic acid, a carboxylic acid anhydride, or a carboxylic halide is used is shown as Formula (3) below.

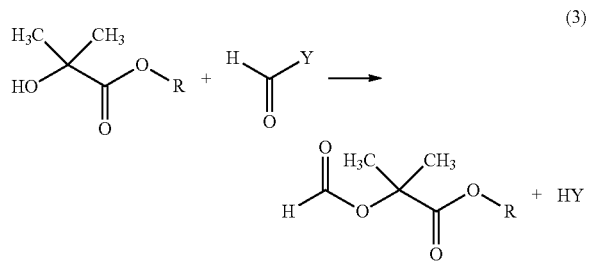

(3)

In Formula (3), R represents a linear, branched, or cyclic alkyl group having 1 to 6 carbon atoms. Y depends on the type of the formylating agent and represents, for example, a hydroxyl group, a formyloxy group, an acetoxy group, chlorine, bromine, iodine, or the like.

Further, a target α-formyloxyisobutyric ester can be produced by transesterifying an α-formyloxyisobutyric ester with an alcohol of different kinds in the presence of a catalyst. The reaction formula for this reaction is shown as Formula (4) below.

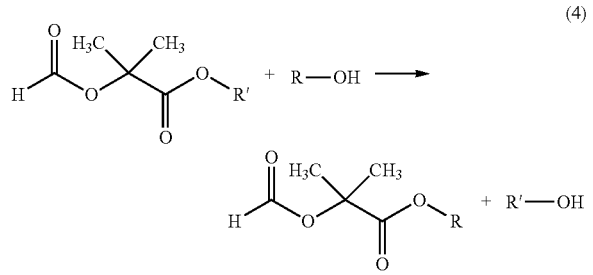

(4)

In Formula (4), R represents a linear, branched, or cyclic alkyl group having 1 to 6 carbon atoms. R' is not particularly limited as long as it is an alkyl group different from R.

Similarly, a target α-formyloxyisobutyric ester can be produced by esterifying α-formyloxyisobutyric acid with an alcohol in the presence of a catalyst. The reaction formula for this reaction is shown as Formula (5) below.

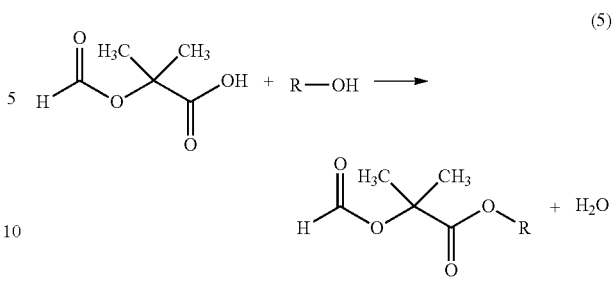

(5)

In Formula (5), R represents a linear, branched, or cyclic alkyl group having 1 to 6 carbon atoms.

Known catalysts, reaction methods, reaction conditions, and reaction apparatus can be used as the catalyst, reaction method, reaction conditions, reaction apparatus, and the like to be used for these reactions, and there are no particular limitation thereon. In addition, as a method for purifying the isobutyric ester according to an embodiment of the present invention represented by Formula (2) and the compound represented by Formula (1) obtained, a known purification method can be used, and there is no limitation thereon.

EXAMPLES

Hereinafter, the present invention will be described in further detail with reference to examples, but the present invention is not limited to these examples.

The reaction performance was evaluated according to the following expression. Reaction yield (%)=[(number of moles of product ester in reaction solution)/(number of moles of raw material ester in solution fed)]×100%

Gas Chromatography (GC) Analysis Conditions

Apparatus: GC-2010 (available from Shimadzu Corporation, trade name)
Detector: FID
Column: DB-1 (capillary column available from J&W Scientific, Inc., trade name) (0.25 mmφ×60 m×0.25 μm)

NMR Spectrum Analysis

Identification of the ester was performed by $^1$H-NMR measurement and $^{13}$C-NMR measurement. The measurement conditions are shown below.
Apparatus: ECA500 (available from JEOL Ltd., trade name)
[$^1$H-NMR]
 Nuclide: $^1$H
 Measurement frequency: 500 MHz
 Measurement sample: 5% CDCl$_3$ solution
[$^{13}$C-NMR]
 Nuclide: $^{13}$C
 Measurement frequency: 125 MHz
 Measurement sample: 5% CDCl$_3$ solution Gas Chromatograph-Mass Spectrometry (GC-MS Analysis)

Identification of the compounds was also performed by determining the molecular weight by GC-MS measurement (chemical ionization method [CI+], high resolution mass spectrometry [millimass]). The measurement conditions are shown below.

GC apparatus: Agilent 7890A (available from Agilent Technologies, trade name)

GC measurement conditions

Column: DB-1 (capillary column available from J&W Scientific, Inc., trade name) (0.25 mmφ×30 m×0.25 μm)

MS apparatus: JMS-T100GCV (available from JEOL Ltd., trade name)

MS measurement conditions: chemical ionization method

Detector conditions: 200 eV, 300 μA

Reagent gas: isobutane

The exact mass values of fragments detected in the protonated state by the chemical ionization method and the chemical composition formula thus attributed were described.

Product Isolation by Chromatograph Method

Materials described below were used for product isolation by a chromatograph method.

Filler: Wakogel C-200 (available from Wako Pure Chemical Industries, Ltd., trade name)

Development solvent: ethyl acetate-hexane

Example 1: Synthesis of Methyl α-Formyloxyisobutyrate 20.0 g of methyl α-hydroxyisobutyrate (available from Mitsubishi Gas Chemical Company, Inc.), 57.0 g of acetic anhydride (available from Wako Pure Chemical Industries, Ltd.), 25.7 g of formic acid (available from Wako Pure Chemical Industries, Ltd.), and 5.3 g of pyridine (available from Wako Pure Chemical Industries, Ltd.) were loaded in a 200-mL glass round bottom flask equipped with a condenser and a stirrer, and reacted under stirring at 0° C. to room temperature for 36 hours. From the GC analysis of the reaction solution, it was confirmed that methyl α-formyloxyisobutyrate was obtained at a reaction yield of 71% by the reaction of the following formula (6) and that no methyl α-acetoxyisobutyrate had been produced. Then, a washing operation was performed three times with a 10% aqueous solution of sodium hydrogen carbonate and twice with a saturated aqueous solution of sodium chloride. The washed product was dried over magnesium sulfate and then concentrated. Subsequently, 13.4 g of methyl α-formyloxyisobutyrate (purity by GC analysis (hereinafter, also referred to as GC purity): 98.6%) was obtained with column chromatograph.

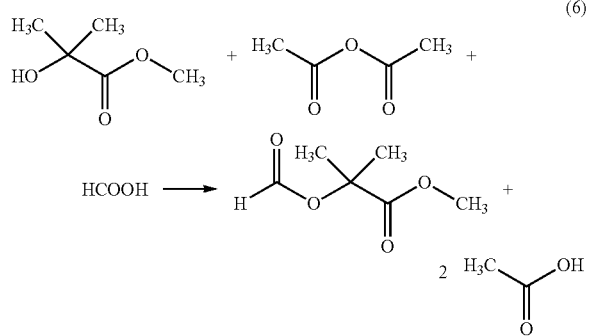

Reference Example 1: Synthesis of Ethyl α-hydroxyisobutyrate

In a 300-mL glass flask equipped with a distillation tube, 56.7 g of methyl α-hydroxyisobutyrate (available from Mitsubishi Gas Chemical Company, Inc.), 33.2 g of ethanol (available from Wako Pure Chemical Industries, Ltd.), and 0.92 g of titanium tetraethoxide (available from Wako Pure Chemical Industries, Ltd.) were loaded. A transesterification reaction was performed under normal pressure with heating and refluxing. The reaction was performed for 96 hours while methanol produced was extracted out of the system. As a result, ethyl α-hydroxyisobutyrate was obtained at a reaction yield of 97%. After water was added to the reaction system to inactivate the catalyst, distillation was performed under reduced pressure to obtain 46.9 g of ethyl α-hydroxyisobutyrate (GC purity: 99.6%) as the fraction at 71 mmHg and 77° C.

Reference Examples 2 to 6: Synthesis of Various α-Hydroxyisobutyric Esters

Using the same reaction apparatus as in Reference Example 1, an appropriate amount of methyl α-hydroxyisobutyrate (available from Mitsubishi Gas Chemical Company, Inc.) was transesterified with a different alcohol (n-propanol, isopropanol, n-butanol, isobutanol, cyclopentanol) in the presence of a suitable catalyst such as a titanium tetraalkoxide and/or sodium alkoxide, and in some cases in the co-presence of a solvent such as hexane or toluene, under appropriate reaction conditions with heating. The transesterification reaction was completed while methanol produced by the reaction was extracted out of the system by distillation or through azeotrope with a reaction solvent under the reaction conditions. The same separation operation as in Reference Example 1 was performed to obtain each of the following α-hydroxyisobutyric esters. The GC purity of the obtained isobutyric ester is also shown.

n-Propyl α-hydroxyisobutyrate (GC purity: 99.8%)
Isopropyl α-hydroxyisobutyrate (GC purity: 99.6%)
n-Butyl α-hydroxyisobutyrate (GC purity: 99.9%)
Isobutyl α-hydroxyisobutyrate (GC purity: 99.6%)
Cyclopentyl α-hydroxyisobutyrate (GC purity: 99.8%)

Examples 2 to 7: Synthesis of Various α-Formyloxyisobutyric Esters

Using a reaction apparatus similar to that of Example 1, a reaction was performed using each α-hydroxyisobutyric ester prepared in Reference Examples 1 to 6, acetic anhydride (available from Wako Pure Chemical Industries, Ltd.), formic acid (available from Wako Pure Chemical Industries, Ltd.), and pyridine (available from Wako Pure Chemical Industries, Ltd.) in appropriate amounts. The operation was performed in the same manner as in Example 1 to obtain each of the following α-formyloxyisobutyric esters with column chromatograph. The GC purity of the resulting esters was described. For novel substances, the results of NMR spectral analysis and GC-MS analysis are also shown.

[Ethyl α-formyloxyisobutyrate]
GC purity: 99.7%

[n-Propyl α-formyloxyisobutyrate]
GC purity: 99.7%
$^1$H NMR (500 MHz, CDCl$_3$) δ 0.94 (3H, t, J=7.5 Hz), 1.61 (6H, s), 1.65-1.69 (2H, m), 4.11 (2H, t, J=7.0 Hz), 7.96 (1H, s)
$^{13}$C NMR (125 MHz, CDCl$_3$) δ 10.2, 21.7, 24.6, 67.0, 78.8, 159.6, 171.9
Exact. Mass 175.10114 (C$_8$H$_{14}$O$_4$, parent peak), 129.09456 (C$_7$H$_{12}$O$_2$)

[Isopropyl α-formyloxyisobutyrate]

GC purity: 99.0%

$^1$H NMR (500 MHz, CDCl$_3$) δ 1.25 (6H, d, J=6.5 Hz), 1.59 (6H, s), 5.06 (1H, sept, J=6.5 Hz), 7.95 (1H, s)

$^{13}$C NMR (125 MHz, CDCl$_3$) δ 21.4, 24.4, 69.0, 78.8, 159.5, 171.3

Exact. Mass 175.10092 (C$_8$H$_{14}$O$_4$, parent peak), 133.05323 (C$_5$H$_9$O$_4$)

[n-Butyl α-formyloxyisobutyrate]

GC purity: 99.9%

$^1$H NMR (500 MHz, CDCl$_3$) δ 0.94 (3H, t, J=7.5 Hz), 1.36-1.40 (2H, m), 1.60 (s, 6H), 1.61-1.64 (2H, m), 4.15 (2H, t, J=7.0 Hz), 7.96 (1H, s)

$^{13}$C NMR (125 MHz, CDCl$_3$) δ 13.6, 19.0, 24.6, 30.4, 65.3, 78.8, 159.6, 171.9

Exact. Mass 189.11665 (C$_9$H$_{16}$O$_4$, parent peak), 143.11054 (C$_8$H$_{14}$O$_2$)

[Isobutyl α-formyloxyisobutyrate]

GC purity: 99.5%

$^1$H NMR (500 MHz, CDCl$_3$) δ 0.94 (6H, d, J=7.0 Hz), 1.61 (6H, s), 1.96 (1H, m), 3.93 (2H, d, J=7.0 Hz), 7.97 (1H, s)

$^{13}$C NMR (125 MHz, CDCl$_3$) δ 18.9, 24.6, 27.6, 71.5, 78.9, 159.6, 171.9

Exact. Mass 189.11679 (C$_9$H$_{16}$O$_4$, parent peak), 143.11040 (C$_8$H$_{14}$O$_2$)

[Cyclopentyl α-formyloxyisobutyrate]

GC purity: 99.4%

$^1$H NMR (500 MHz, CDCl$_3$) δ 1.58 (6H, s), 1.58-1.63 (2H, m), 1.66-1.75 (4H, m), 1.80-1.88 (2H, m), 5.21 (1H, m), 7.95 (1H, s)

$^{13}$C NMR (125 MHz, CDCl$_3$) δ 22.6, 24.5, 32.3, 78.4, 78.9, 159.5, 171.5

Exact. Mass 201.11628 (C$_{10}$H$_{16}$O$_4$, parent peak), 133.05459 (C$_5$H$_8$O$_4$)

The results of aroma evaluation performed by perfumers for the various α-formyloxyisobutyric esters obtained by the method described above are shown in Table 1.

TABLE 1

| | Structural formula | Aroma evaluation |
|---|---|---|
| Example 1 | (structure) | Fruity aroma<br>Woody aroma having floralness (damascone-like)<br>Green aroma<br>Amber aroma having balsamicness |
| Example 2 | (structure) | Coconut-like sweet and fruity aroma<br>Mint-like aroma having floralness<br>Herbal aroma |
| Example 3 | (structure) | Fresh mint-like aroma<br>Fruity aroma<br>Bitter citrus aroma<br>Anise-like spicy aroma<br>Herbal aroma |
| Example 4 | (structure) | Fruity aroma<br>Floral aroma<br>Amber aroma having an earthy nuance<br>Woody aroma |
| Example 5 | (structure) | Fresh mint-like aroma<br>Sweet fruity aroma |
| Example 6 | (structure) | Fresh mint-like aroma<br>Coconut-like fruity aroma<br>Jasmine-like spicy aroma<br>Lilac-like floral aroma<br>Myrrha-based rose-like floral aroma |
| Example 7 | (structure) | Fresh mint-like aroma<br>Rose-like floral aroma<br>Grapefruit-like bitter citrus aroma |

Biodegradability Evaluation of Fragrance Material

One of methods for evaluating biodegradability of a compound is the OECD test guideline 301 C. In accordance with the method, assessment of biodegradability is possible for the compound from the biochemical oxygen demand and the actual rate of oxygen uptake in an aqueous solution in which the compound and aerobic microorganisms coexist.

Calculation software "Biowin5" and "Biowin6" is known and used in a method for easily and accurately estimating the probability of biodegradation of the compound in compliance with this test method.

The software is available to the public as one of modules of calculation software called "The Estimations Programs Interface for Windows version 4.1", created by the United States Environmental Protection Agency (EPA) for the purpose of evaluating the environmental effects of chemical substances, and is used in the compound classification for The Globally Harmonized System of Classification and Labelling of Chemicals (GHS) and the review of new chemical substances by the United States Environmental Protection Agency. This software was used to evaluate the difference in biodegradability between existing fragrance materials and the compounds according to an embodiment of the present invention.

Menthol, menthone, and carvone, having a mint-like note and (E)-α-damascone and (E)-β-damascenone, having a fruity note, were selected as representative examples of existing fragrance materials similar to the compounds according to an embodiment of the present invention, and evaluated along with the compounds according to an embodiment of the present invention. The SMILES formulas used for input to the software and the output results of the probabilities of good degradability by "Biowin5 (linear prediction model)" and "Biowin6 (non-linear prediction model)" are shown in Tables 2 to 3. A larger value of the results indicates better degradability: for a value of 0.5 or more, the compound was rated as having good degradability (symbol "A" in the table), and for a value of less than 0.5, the compound was rated as having low degradability (symbol "B" in the table).

From Table 2 to Table 3, the results obtained show that the compounds according to an embodiment of the present invention were expected to have good biodegradability with respect to menthol, menthone, carvone, (E)-α-damascone, and (E)-β-damascenone, which were the existing fragrance materials similar to the compounds according to an embodiment of the present invention. The results indicated that the compounds according to an embodiment of the present invention are easily biodegraded after being released into the environment as fragrances, and thus exhibited a lower impact on the environment.

TABLE 2

| | | | Biowin5 | | Biowin 6 | |
| --- | --- | --- | --- | --- | --- | --- |
| Example | Structural formula | SMILES | Degradation probability | Score | Degradation probability | Score |
| 1 | | COC(C(C)(C)OC=O)=O | 1.034 | A | 0.975 | A |
| 2 | | CC(C(OCC)=O)(C)OC=O | 1.041 | A | 0.975 | A |
| 3 | | CC(C(OCCC)=O)(C)OC=O | 1.049 | A | 0.976 | A |
| 4 | | CC(C(OC(C)C)=O)(C)OC=O | 0.900 | A | 0.941 | A |
| 5 | | CC(C(OCCCC)=O)(C)OC=O | 1.057 | A | 0.977 | A |
| 6 | | CC(C(OCC(C)C)=O)(C)OC=O | 0.908 | A | 0.942 | A |

TABLE 2-continued

| Example | Structural formula | SMILES | Biowin5 Degradation probability | Score | Biowin 6 Degradation probability | Score |
| --- | --- | --- | --- | --- | --- | --- |
| 7 | (cyclopentyl α-formyloxyisobutyrate structure) | CC(C(OC1CCCC1)=O)(C)OC=O | 0.964 | A | 0.947 | A |

TABLE 3

| Comparative Example | Structural formula | SMILES | Biowin5 Degradation probability | Score | Biowin6 Degradation probability | Score |
| --- | --- | --- | --- | --- | --- | --- |
| 1 | (Menthol) | CC(C)C1CCC(C)CC1O | 0.455 | B | 0.331 | B |
| 2 | (Menthone) | CC(C)C1CCC(C)CC1=O | 0.406 | B | 0.335 | B |
| 3 | (Carvone) | C=C(C)C(C1)CC=C(C)C1=O | 0.454 | B | 0.375 | B |
| 4 | ((E)-alpha-damascone) | CC1(C)C(C(/C=C/C)=O)C(C)=CCC1 | 0.398 | B | 0.216 | B |
| 5 | ((E)-beta-damascenone) | CC1(C)C(C(/C=C/C)=O)C(C)C=CC1 | 0.378 | B | 0.213 | B |

Example 8: Floral Bouquet-Type Fragrance Composition

A fragrance composition was prepared by adding 22.9 parts by mass of the cyclopentyl α-formyloxyisobutyrate obtained in Example 7 to 77.1 parts by mass of a fragrance composition having a composition shown in Table 4.

According to the aroma evaluation by perfumers, addition of the cyclopentyl α-formyloxyisobutyrate of Example 7 to the fragrance composition having the composition described in Table 4 totally softened green and eugenol and provided a feeling of integrity. As a result, provided was a fragrance composition having a natural and elegant carnation-like floral bouquet aroma, to which a soft rose-like floralness and fresh and crisp citrusness were imparted. The aroma of this fragrance composition seems to be suitable for perfuming foundation, deodorant powder, and the like.

TABLE 4

| Blend ingredients | parts by mass |
| --- | --- |
| Phenethyl alcohol | 13.1 |
| 4-tert-Butylcyclohexyl acetate | 11.7 |
| Hexyl salicylate | 11.1 |
| Sandalwood oil (10%) | 10.9 |
| Lemon oil | 10.7 |
| Linalool | 5.3 |
| Limonene | 5.2 |
| Nerol | 2.7 |
| Rosewood oil (10%) | 2.7 |
| Phenylacetaldehyde dimethyl acetal | 2.4 |
| Eugenol | 1.2 |
| Total | 77.1 |

*Blend ingredients in parentheses in the table were used as a solution diluted with dipropylene glycol. The figures represent mass % of the fragrance included in the solution.

Example 9: Floral-Type Fragrance Composition

A fragrance composition was prepared by adding 32.2 parts by mass of the isopropyl α-formyloxyisobutyrate obtained in Example 4 to 67.8 parts by mass of a fragrance composition having a composition shown in Table 5.

According to the aroma evaluation by perfumers, addition of the isopropyl α-formyloxyisobutyrate of Example 4 to the fragrance composition having the composition described in Table 5 totally added woodiness to thereby emphasize fruitiness and floralness and provide a feeling of brisk integrity. As a result, obtained was a fragrance composition having a powdery and elegant woody and floral aroma, to which floralness and woodiness were imparted. The aroma of this fragrance composition seems to be suitable for perfuming foundation, deodorant powder, skin lotion, milky lotion, and the like.

TABLE 5

| Blend ingredients | parts by mass |
| --- | --- |
| Coumarin (5%) | 16.0 |
| Geraniol | 9.2 |
| Cyclopentadecanone (25%) | 8.6 |
| Orange sweet oil (10%) | 8.3 |
| 2-Phenylethyl alcohol | 5.3 |
| Limonene | 4.6 |
| Lavender oil (10%) | 4.2 |
| Benzyl acetate (10%) | 3.2 |
| Linalool | 2.9 |
| γ-Undecalactone | 2.3 |
| Lemon oil | 2.2 |
| Ylang ylang oil | 1.0 |
| Total | 67.8 |

*Blend ingredients in parentheses in the table were used as a solution diluted with dipropylene glycol. The figures represent mass % of the fragrance included in the solution.

INDUSTRIAL APPLICABILITY

An isobutyric ester compounds having a formyloxy group at the α-position according to an embodiment of the present invention has an excellent aroma and is expected to be used itself as a fragrance. Additionally, use of the compound as a fragrance ingredient can provide a fragrance composition excellent in aroma properties. The composition, when blended in a variety of products, exhibits desired perfuming properties.

Furthermore, it was shown that the compounds obtained in Examples each have excellent biodegradability and a low impact on the environment and are suitable for use.

The invention claimed is:

1. A fragrance composition comprising a compound represented by the following formula (1) as an active ingredient:

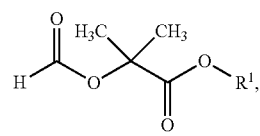

(1)

wherein $R^1$ is selected from the group consisting of an ethyl group, a n-propyl group, an isopropyl group, a n-butyl group, an isobutyl group, and a cyclopentyl group.

2. A compound, represented by the following formula (2):

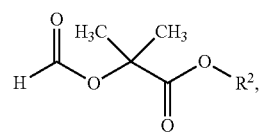

(2)

wherein $R^2$ represents a straight, branched, or cyclic alkyl group having 3 to 6 carbon atoms.

3. The compound according to claim 2, wherein $R^2$ is selected from the group consisting of a n-propyl group, an isopropyl group, a n-butyl group, an isobutyl group, and a cyclopentyl group.

4. The compound according to claim 2, wherein $R^2$ is a n-propyl group.

5. The compound according to claim 2, wherein $R^2$ is an isopropyl group.

6. The compound according to claim 2, wherein $R^2$ is a n-butyl group.

7. The compound according to claim 2, wherein $R^2$ is an isobutyl group.

8. The compound according to claim 2, wherein $R^2$ is a cyclopentyl group.

9. The fragrance composition according to claim 1, wherein the compound of the formula (1) imparts a mint-like scent or an amber aroma having an earthy nuance.

* * * * *